(12) United States Patent
Takahashi et al.

(10) Patent No.: US 9,796,678 B2
(45) Date of Patent: Oct. 24, 2017

(54) METHOD FOR MANUFACTURING OPTICALLY ACTIVE COMPOUND

(71) Applicant: SUMITOMO CHEMICAL COMPANY, LIMITED, Tokyo (JP)

(72) Inventors: Tomoaki Takahashi, Oita (JP); Satoru Ujita, Hyogo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/124,177

(22) PCT Filed: Mar. 6, 2015

(86) PCT No.: PCT/JP2015/057395
§ 371 (c)(1),
(2) Date: Sep. 7, 2016

(87) PCT Pub. No.: WO2015/141564
PCT Pub. Date: Sep. 24, 2015

(65) Prior Publication Data
US 2017/0022162 A1     Jan. 26, 2017

(30) Foreign Application Priority Data
Mar. 18, 2014 (JP) ................. 2014-054457

(51) Int. Cl.
| C07D 215/08 | (2006.01) |
| C07D 215/04 | (2006.01) |
| C07B 53/00 | (2006.01) |
| C07D 215/06 | (2006.01) |

(52) U.S. Cl.
CPC ............ *C07D 215/08* (2013.01); *C07B 53/00* (2013.01); *C07D 215/04* (2013.01); *C07D 215/06* (2013.01)

(58) Field of Classification Search
CPC .. C07D 215/04; C07D 215/06; C07D 215/08; C07B 53/00
See application file for complete search history.

(56) References Cited

U.S. PATENT DOCUMENTS

| 4,087,561 A * | 5/1978 | Bharucha ................. A23B 4/02 |
| | | 426/266 |
| 5,521,317 A | 5/1996 | Briner |
| 2002/0062027 A1 | 5/2002 | Pfaltz et al. |

OTHER PUBLICATIONS

Nishimura, CA 149:245905, abstract only of e-EROS encyclopedia of reagents for organic Synthesis, 2001.*
Wu, CHemm COmmun, 2013, 49, 7052-7054.*
International Search Report dated Jun. 9, 2015 in corresponding International (PCT) Application No. PCT/JP2015/057395.

Written Opinion of the International Searching Authority dated Jun. 9, 2015 in corresponding International (PCT) Application No. PCT/JP2015/057395.
Sumerin et al., Highly Active Metal-Free Catalysts for Hydrogenation of Unsaturated Nitrogen-Containing Compounds, Advanced Synthesis & Catalysis, vol. 353, No. 11-12, 2011, p. 2093-2110.
Oka et al., "Synthesis and characterization of poly(1,3-phenylene)-based polyradicals carrying cyclic aminoxyls", Journal of Materials Chemistry, vol. 11, No. 5, 2001, p. 1364-1369.
Rybakov et al., 6-Ethoxy-1,2,3,4-tetrahydro-2,2,4-trimethylquinoline, Acta Crystallographica, Section E; Structure Reports Online, vol. 60, No. 7, 2004, p. o1145-o1146.
Miyazaki et al., "Biological and Pharmacological Activities of Optically Active Drugs and their Candidates", Edited by the Chemical Society of Japan, Japan Scientific Societies Press, 1989, p. 16-29 and 212-225, partial English translation.
Edited by Nagano et al., "7.2 Actual Drug Design", Medicinal Chemistry, 2004, p. 163-168, partial English translation.
Wermuth et al., "The Practice of Medicinal Chemistry", The Chemical Society of Japan, vol. 1, 1998, p. 475-501.
Tang et al., "New Chiral Phosphorus Ligands for Enantioselective Hydrogenation", Chemical Reviews, vol. 103, No. 8, 2003, p. 3029-3069.

(Continued)

*Primary Examiner* — D M Seaman
(74) *Attorney, Agent, or Firm* — Wenderoth, Lind & Ponack, L.L.P.

(57) ABSTRACT

The present invention provides a method for manufacturing an optically active compound of formula (2), which contains bringing hydrogen into contact with a compound of formula (1) in the presence of a transition metal catalyst having an optically active ligand. In the formula, $R^1$ represents a hydrogen atom or an acetyl group, $R^2$, $R^3$, $R^4$, and $R^5$ each independently represents a hydrogen atom, a halogen atom, an alkyl group, an alkoxy group, a hydroxy group, a nitro group, an amino group, or an acyl group, $R^6$ represents an alkyl group, $R^7$ and $R^8$ each independently represents a hydrogen atom or an alkyl group, and a carbon atom marked with an asterisk (*) represents an asymmetric carbon atom.

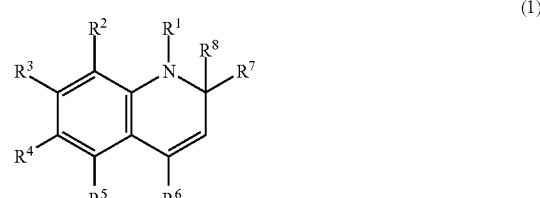

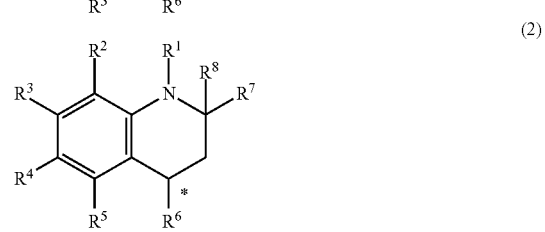

6 Claims, No Drawings

(56) References Cited

OTHER PUBLICATIONS

Smidt et al., "SimplePHOX, a Readily Available Chiral Ligand System for Iridium-Catalyzed Asymmetric Hydrogenation", Organic Letters, vol. 6, No. 12, 2004, p. 2023-2026.
Baeza et al., "Iridium-Catalyzed Asymmetric Hydrogenation of N-Protected Indoles", Chemistry—A European Journal, vol. 16, No. 7, 2010, p. 2036-2039.
Church et al., "Enantioselectivity in the Iridium-Catalyzed Hydrogenation of Unfunctionalized Olefins", Organometallics, vol. 29, No. 24, 2010, p. 6769-6781.
Nanchen et al., "Synthesis and Application of Chiral N-Heterocyclic Carbene-Oxazoline Ligands: Iridium-Catalyzed Enantioselective Hydrogenation", Chemistry—A European Journal, vol. 12, No. 17, 2006, p. 4550-4558.
Goulioukina et al., "Highly enantioselective hydrogenation of $\alpha,\beta$-unsaturated phosphonates with iridium-phosphinooxazoline complex: synthesis of a phosphorus analogue of naproxen", Tetrahedron: Asymmetry, vol. 14, No. 10, 2003, p. 1397-1401.
Ohta et al., "BINAP-Ru(II) and BINAP-Rh(I)-catalyzed asymmetric hydrogenation of olefins without heteroatom-functionalities", Journal of Organometallic Chemistry, vol. 502, 1995, p. 169-176.
Forman et al., "Asymmetric hydrogenation of $\alpha$-ethylstyrenes catalyzed by chiral ruthenium complexes", Tetrahedron Letters, vol. 41, 2000, p. 9471-9475.

\* cited by examiner

METHOD FOR MANUFACTURING OPTICALLY ACTIVE COMPOUND

TECHNICAL FIELD

The present invention relates to a method for manufacturing an optically active compound which is useful as an intermediate for the synthesis of pharmaceuticals, pesticides, and the like.

BACKGROUND ART

Patent Document 1 mentions a method for manufacturing a compound of formula (III):

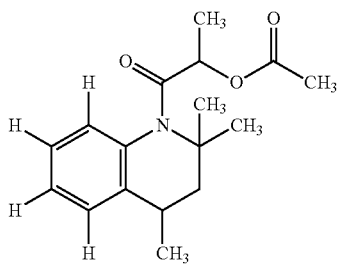

(III)

the method containing mixing a compound of formula (II):

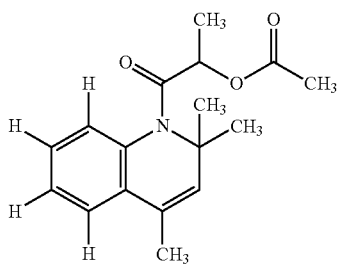

(II)

a palladium/carbon catalyst, and hydrogen, and also mentions 1,2-dihydro-2,2,4-trimethylquinoline as a raw material of the compound of formula (II).

PRIOR ART DOCUMENT

Patent Document

Patent Document 1: JP H7-215921 A

SUMMARY OF THE INVENTION

Problems to be Solved by the Invention

There has never been known a method in which a compound of formula (1):

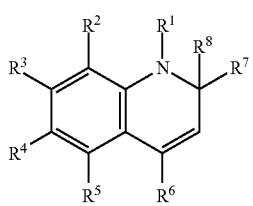

(1)

wherein $R^1$ represents a hydrogen atom or an acetyl group, $R^2$, $R^3$, $R^4$, and $R^5$ each independently represents a hydrogen atom, a halogen atom, an alkyl group, an alkoxy group, a hydroxy group, a nitro group, an amino group, or an acyl group, $R^6$ represents an alkyl group, and $R^7$ and $R^8$ represent hydrogen or an alkyl group, such as 1,2-dihydro-2,2,4-trimethylquinoline, is subjected to asymmetric hydrogenation to manufacture an optically active compound of formula (2):

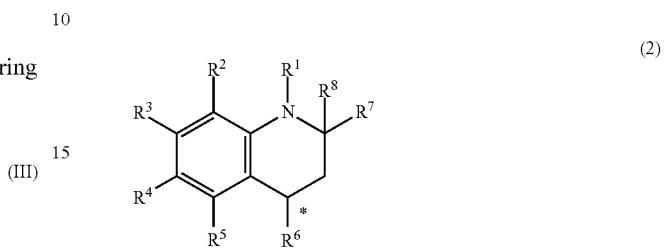

(2)

wherein $R^1$, $R^2$, $R^3$, $R^4$, $R^5$, $R^6$, $R^7$, and $R^8$ are the same as defined above, and a carbon atom marked with an asterisk (*) represents an asymmetric carbon atom.

Means for Solving the Problems

The present invention provides a method for manufacturing an optically active compound, which comprises subjecting a prochiral compound to asymmetric hydrogenation.

The present invention includes the following inventions.

[1] A method for manufacturing an optically active compound of formula (2):

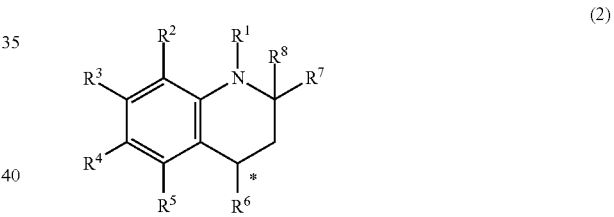

(2)

wherein $R^1$, $R^2$, $R^3$, $R^4$, $R^5$, $R^6$, $R^7$, and $R^8$ are the same as defined below, and a carbon atom marked with an asterisk (*) represents an asymmetric carbon atom, which comprises bringing hydrogen into contact with a compound of formula (1):

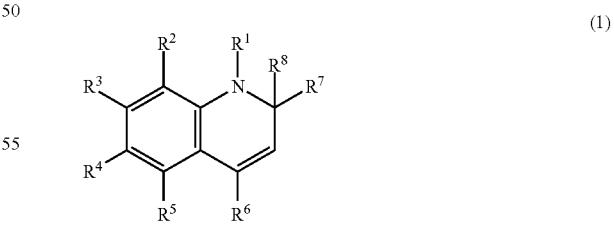

(1)

wherein $R^1$ represents a hydrogen atom or an acetyl group, $R^2$, $R^3$, $R^4$, and $R^5$ each independently represents a hydrogen atom, a halogen atom, an alkyl group, an alkoxy group, a hydroxy group, a nitro group, an amino group, or an acyl group, $R^6$ represents an alkyl group, and $R^7$ and $R^8$ each independently represents a hydrogen atom or an alkyl group, in the presence of a transition metal catalyst having an optically active ligand.

[2] The manufacturing method according to [1], wherein $R^6$ is a methyl group or an ethyl group, and $R^7$ and $R^8$ are each independently a hydrogen atom, a methyl group, or an ethyl group.
[3] The manufacturing method according to [1] or [2], wherein $R^6$, $R^7$, and $R^8$ are methyl groups, and $R^2$, $R^3$, $R^4$, and $R^5$ are hydrogen atoms.
[4] The manufacturing method according to any one of [1] to [3], wherein the transition metal catalyst having an optically active ligand is an iridium catalyst having an optically active ligand, a rhodium catalyst having an optically active ligand, or a ruthenium catalyst having an optically active ligand.
[5] The manufacturing method according to any one of [1] to [4], wherein hydrogen is brought into contact with the compound of formula (1) at a temperature in a range of 20 to 100° C.
[6] The manufacturing method according to any one of [1] to [5], wherein hydrogen is brought into contact with the compound of formula (1) under a gauge pressure in a range of 0.1 MPa to 20 MPa.

Effects of the Invention

According to the invention, it is possible to manufacture an optically active compound of formula (2) by subjecting a compound of formula (1) to asymmetric hydrogenation.

MODE FOR CARRYING OUT THE INVENTION

Substituents $R^1$, $R^2$, $R^3$, $R^4$, $R^5$, $R^6$, $R^7$, and $R^8$ of the above-mentioned compounds of formula (1) and formula (2) will be described below.

Examples of the halogen atom represented by $R^2$, $R^3$, $R^4$, or $R^5$ include a fluorine atom, a chlorine atom, a bromine atom, and an iodine atom.

Examples of the alkyl group represented by $R^2$, $R^3$, $R^4$, or $R^5$ include alkyl groups having 1 to 4 carbon atoms, such as a methyl group, an ethyl group, an n-propyl group, an isopropyl group, an n-butyl group, an isobutyl group, a sec-butyl group, and a tert-butyl group. Of these alkyl groups, a methyl group or an ethyl group is preferable.

Examples of the alkoxy group represented by $R^2$, $R^3$, $R^4$, or $R^5$ include alkoxy groups having 1 to 4 carbon atoms, such as a methoxy group, an ethoxy group, an isopropoxy group, and a tert-butoxy group. Of these, a methoxy group or an ethoxy group is preferable.

Examples of the acyl group represented by $R^2$, $R^3$, $R^4$, or $R^5$ include acyl groups having 2 to 7 carbon atoms, such as an acetyl group, a propionyl group, and a benzoyl group. Of these acyl groups, an acetyl group is preferable.

$R^2$, $R^3$, $R^4$, and $R^5$ are preferably the same groups, and more preferably hydrogen atoms.

$R^6$ is preferably a methyl group or an ethyl group, and more preferably a methyl group.

$R^7$ and $R^8$ are preferably the same groups.

Preferably, $R^7$ and $R^8$ are each independently a hydrogen atom, a methyl group, or an ethyl group, and more preferably a methyl group.

Examples of the compound of formula (1) (hereinafter sometimes referred to as the compound (1)) include a compound of formula (1-1) to a compound of formula (1-20). Of these compounds, a compound of formula (1-1), formula (1-5), formula (1-9), formula (1-11), formula (1-15), or formula (1-19) is preferable, and a compound of formula (1-1) or a compound of formula (1-11) is more preferable:

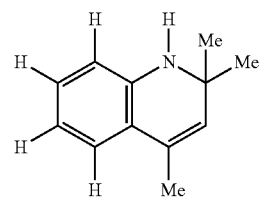 (1-1)

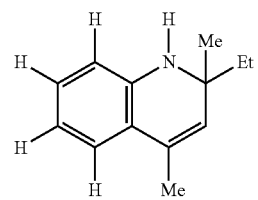 (1-2)

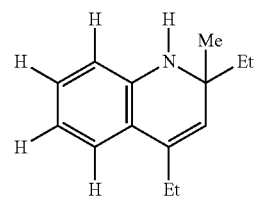 (1-3)

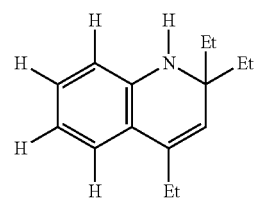 (1-4)

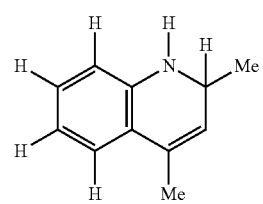 (1-5)

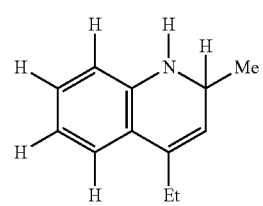 (1-6)

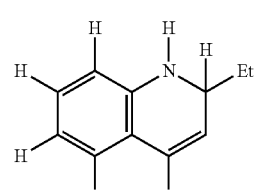 (1-7)

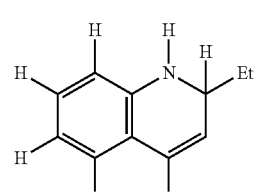 (1-8)

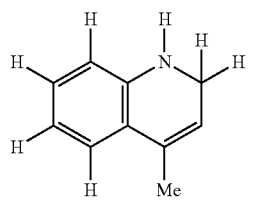
(1-9)

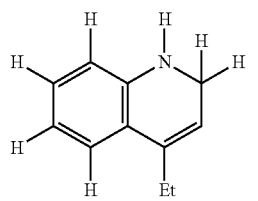
(1-10)

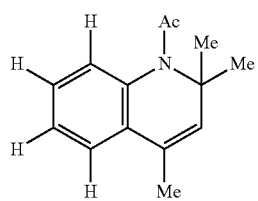
(1-11)

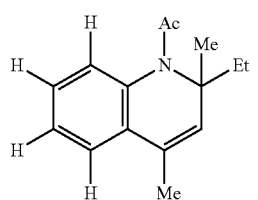
(1-12)

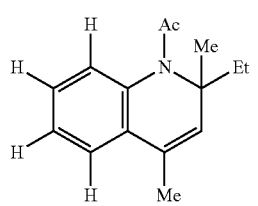
(1-13)

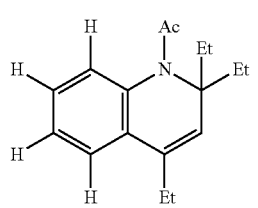
(1-14)

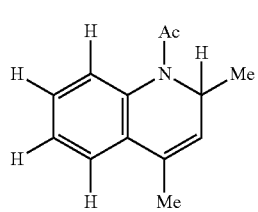
(1-15)

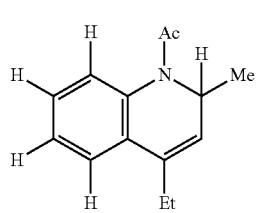
(1-16)

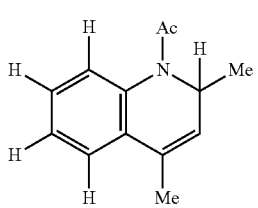
(1-17)

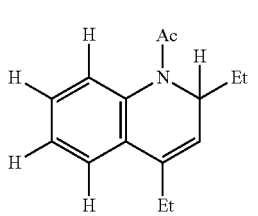
(1-18)

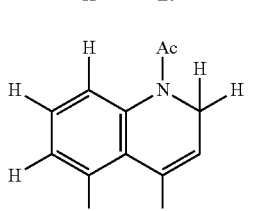
(1-19)

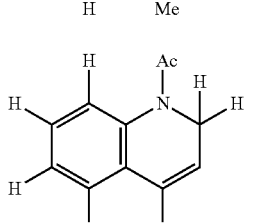
(1-20)

wherein Me represents a methyl group, Et represents an ethyl group, and Ac represents an acetyl group.

The compound (1) can be manufactured, for example, by the method mentioned in J. Chem. Soc. (C), 1966, 514-517. Commercially available products may be used as the compound (1).

Examples of the optically active compound of formula (2) (hereinafter sometimes referred to as the compound (2)) include a compound of formula (2-1) to an optically active compound of formula (2-20).

The compound (2) is preferably a compound of formula (2-1), formula (2-5), formula (2-9), formula (2-11), formula (2-15), or formula (2-19), and more preferably a compound of formula (2-1) or a compound of formula (2-11).

Optical purity of the compound (2) is preferably in a range of 5 to 100% ee:

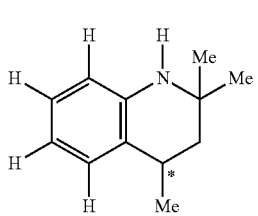
(2-1)

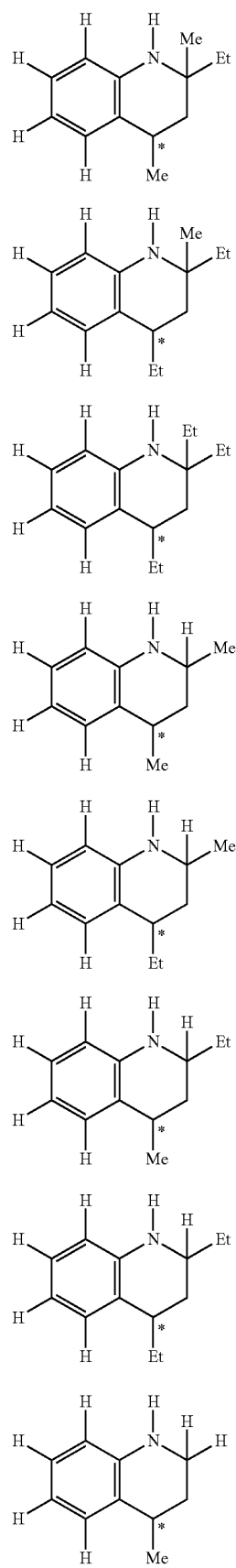
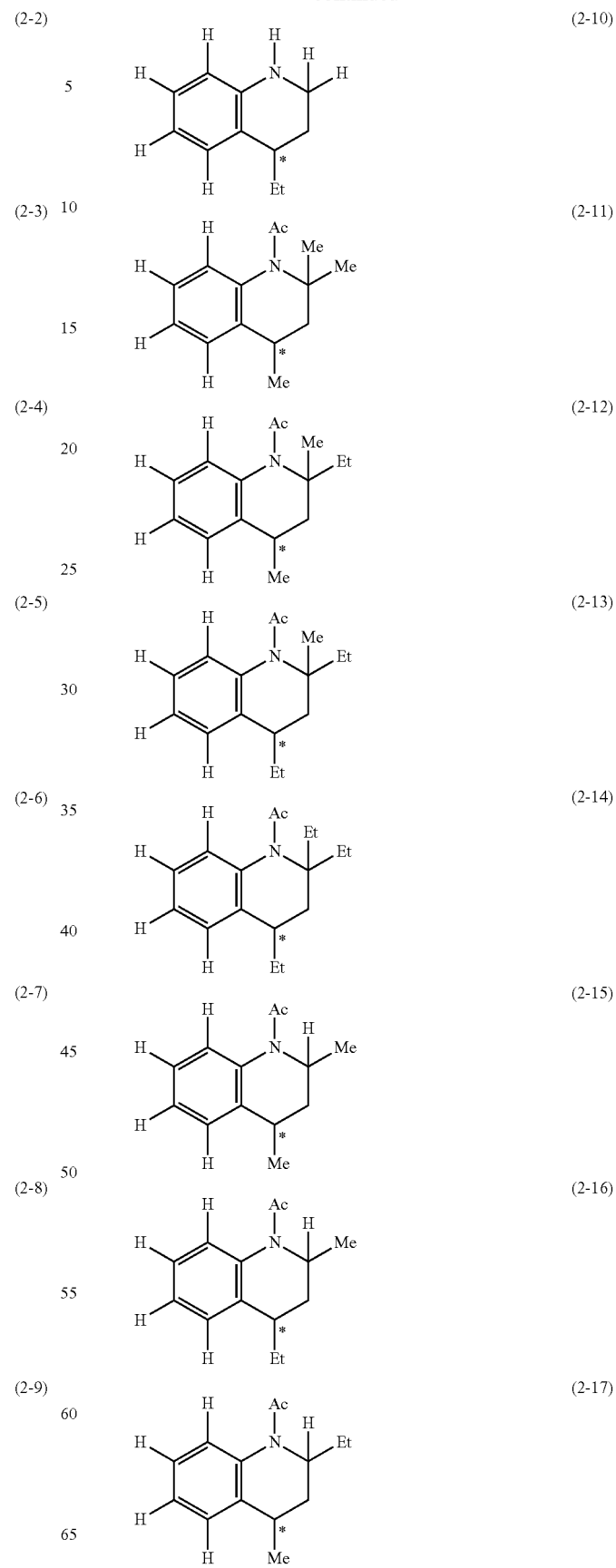

-continued

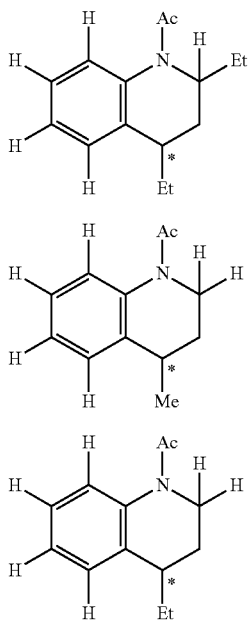

(2-18)

(2-19)

(2-20)

wherein Me represents a methyl group, Et represents an ethyl group, Ac represents an acetyl group, and a carbon atom marked with an asterisk (*) represents an asymmetric carbon atom.

The transition metal catalyst having an optically active ligand (hereinafter sometimes referred to as a transition metal catalyst) is preferably a ruthenium catalyst having an optically active ligand, an iridium catalyst having an optically active ligand, and a rhodium catalyst having an optically active ligand. The optically active ligand is preferably a chiral phosphine ligand, a chiral phosphinate ligand, a chiral phosphite ligand, a chiral phosphinous amide ligand, and a chiral phosphonous diamide ligand.

Hereinafter, L represents an optically active ligand, cod represents 1,5-cyclooctadien, nbd represents norbornadiene, DPEN represents 1,2-diphenylethylenediamine, DAIPEN represents 1,1-di(µ-methoxyphenyl)-2-isopropylethylenediamine, dmf represents dimethylformamide, DPEN represents 1,2-diphenylethylenediamine, Me represents a methyl group, Et represents an ethyl group, Ac represents an acetyl group, Ph represents a phenyl group, and Tf represents a trifluoromethylsulfonyl group.

Examples of L in the rhodium catalyst and the ruthenium catalyst include 2,2'-bis(diphenylphosphino)-1,1'-binaphthyl [hereinafter sometimes referred to as BINAP], 2,2'-bis(di(µ-tolylphosphino)-1,1'-binaphthyl) [hereinafter sometimes referred to as p-Tol-BINAP], 2,2'-bis(di(3.5-xylyl)phosphino)-1,1'-binaphthyl [hereinafter sometimes referred to as DM-BINAP], 2,2'-bis(di(3,5-di-tert-butyl phenyl)phosphino)-1,1'-binaphthyl [T-Bu-2-BINAP], 2,2'-bis[di(4-methoxy-3,5-dimethylphenyl)phosphino]-1,1'-binaphthyl [hereinafter sometimes referred to as DMM-BINAP], 2,2'-bis(dicyclo pentylphosphino)-1,1'-binaphthyl [Cp-BINAP], ((5,6),(5',6')-bis(methylendioxy)biphenyl-2,2'-diyl)bis(diphenylphosphine) [hereinafter sometimes referred to as SEGPHOS], ((5,6),(5',6')-bis(methylenedioxy)biphenyl-2,2'-diyl)bis(di-p-tolylphosphine) [hereinafter sometimes referred to as p-Tol-SEGPHOS], ((5,6),(5',6')-bis(methylenedioxy)biphenyl-2,2'-diyl)bis(di-3,5-xylyl phosphine) [hereinafter sometimes referred to as DM-SEGPHOS], ((5,6), (5',6')-bis(methylenedioxy)biphenyl(2,2'-diyl)bis(di-4-methoxy-3,5-dimethylphenylphosphine) [hereinafter sometimes referred to as DMM-SEGPHOS], ((5,6),(5',6')-bis(methylenedioxy)biphenyl-2,2'-diyl)bis(di-4-methoxy-3,5-di-tert-butylphenylphosphine) [hereinafter sometimes referred to as DTBM-SEGPHOS], ((5,6),(5',6')-bis(methylenedioxy)biphenyl-2,2'-diyl)bis(dicyclohexylphosphine) [hereinafter sometimes referred to as Cy-SEGPHOS], 2,2-dimethyl-6,6'-bis(diphenylphosphino)-1,1'-biphenyl [hereinafter sometimes referred to as BIPHEMP], 2,2'-dimethyl-6,6'-bis(di-p-tolylphosphino)-1,1'-biphenyl [hereinafter sometimes referred to as p-Tol-BIPHEMP], 2,2'-dimethyl-6,6'-bis(di-3,5-xylylphosphino)-1,1'-biphenyl [hereinafter sometimes referred to as DM-BIPHEMP], 2,2'-dimethyl-6,6'-bis(di-4-methoxy-3,5-dimethylphenylphosphino)-1,1'-biphenyl [hereinafter sometimes referred to as DMM-BIPHEMP], 2,2'-dimethyl-6,6'-bis(di-4-tert-butoxy-3,5-dimethylphenylphosphino)-1,1'-biphenyl [hereinafter sometimes referred to as DTBM-BIPHEMP], 2,2'-dimethyl-6,6'-bis(dicyclohexylphosphino)-1,1'-biphenyl [hereinafter sometimes referred to as Cy-BIPHEMP], 2,2'-dimethoxy 6,6'-bis(diphenylphosphino)-1,1'-biphenyl [hereinafter sometimes referred to as MeO-BIPHEP], 2,2'-dimethoxy-6,6'-bis(di-p-tolylphosphino)-1,1'-biphenyl [hereinafter sometimes referred to as p-Tol-MeO-BIPHEP], 2,2'-dimethoxy-6,6'-bis(di-3,5-xylylphosphino)-1,1'-biphenyl [hereinafter sometimes referred to as DM-MeO-BIPHEP], 2,2'-dimethoxy-6,6'-bis(di-4-methoxy-3,5-dimethylphenylphosphino)-1,1'-biphenyl [hereinafter sometimes referred to as DMM-MeO-BIPHEP], 2,2'-dimethoxy-6,6'-bis(di-4-tert-butoxy-3,5-dimethylphenylphosphino)-1,1'-biphenyl [hereinafter sometimes referred to as DTBM-MeO-BIPHEP], 2,2'-dimethoxy-6,6'-bis(dicyclohexylphosphino)-1,1'-biphenyl [hereinafter sometimes referred to as Cy-MeO-BIPHEP], 2,2'-dimethyl-3,3'-dichloro-4,4'-dimethyl-6,6'-bis(di-p-tolyl phosphino)-1,1'-biphenyl [hereinafter sometimes referred to as p-Tol-CM-BIPHEMP], 2,2'-dimethyl-3,3'-dichloro-4,4'-dimethyl-6,6'-bis(di-3,5-xylylphosphino)-1,1'-biphenyl [hereinafter sometimes referred to as DM-CM-BIPHEMP], 2,2'-dimethyl-3,3'-dichloro-4,4'-dimethyl-6,6'-bis(di-4-methoxy-3,5-dimethylphenylphosphino)-1,1'-biphenyl [hereinafter sometimes referred to as DMM-CM-BIPHEMP], 1,2-bis(2,5-dimethylphosphino)benzene [hereinafter sometimes referred to as Me-DUPHOS], 1,2-bis(2,5-diethylphosphino)benzene [hereinafter sometimes referred to as Et-DUPHOS], 1,1'-di-tert-butyl-[2,2']-diphosphorane [hereinafter sometimes referred to as TANGPHOS], 2,2'-di-tert-butyl-2,3,2',3'-tetrahydro-1,1'-bi-1H-isophosphenylindole [hereinafter sometimes referred to as DUANPHOS], 2,4-bis(di(3,5-xylyl)phosphinopentane [hereinafter sometimes referred to as XYLSKEWPHOS], and [(5,6),(5', 6')-bis(ethylenedioxy)biphenyl-2,2'-diyl]diphenylphosphine [hereinafter sometimes referred to as SYNPHOS], and BINAP, p-Tol-BINAP, DM-BINAP, T-Bu-2-BINAP, DMM-BINAP, Cp-BINAP, Me-DUPHOS, XYLSKEWPHOS, and DUANPHOS are preferable, and BINAP and Me-DUPHOS are more preferable.

Examples of the rhodium catalyst having an optically active ligand include [Rh(L)Cl]₂, [Rh(L)Br]₂, [Rh(L)I]₂, [Rh(cod)(L)]OTf, [Rh(cod)(L)]BF₄, [Rh(cod)(L)]ClO₄, [Rh(cod)(L)]SbF₆, [Rh(cod)(L)]PF₆, [Rh(cod)(L)]BPh₄, [Rh(nbd)(L)]OTf, [Rh(nbd)(L)]BF₄, [Rh(nbd)(L)]ClO₄, [Rh(nbd)(L)]SbF₆, [Rh(nbd)(L)]PF₆, [Rh(nbd)(L)]BPh₄, [Rh(L)₂]OTf, [Rh(L)₂]BF₄, [Rh(L)₂]ClO₄, [Rh(L)₂]SbF₆, [Rh(L)₂]PF₆, and [Rh(L)₂]BPh₄, and [Rh(L)Cl]₂, [Rh(cod)(L)]BF₄, and [Rh(L)₂]BF₄ are preferable.

Examples of the ruthenium catalyst having an optically active ligand include Ru(OAc)₂(L), Ru(OCOCF₃)₂(L), Ru₂Cl₄(L)₂NEt₃, RuHCl(L), RuHBr(L), RuHI(L), [{RuCl(L)}₂(µ-Cl)₃][Me₂NH₂], [{RuBr(L)}₂(µ-Br)₃][Me₂NH₂], [{RuI(L)}₂(µ-I)₃][Me₂NH₂], [{RuCl(L)}₂(µ-Cl)₃][Et₂NH₂], [{RuBr(L)}₂(µ-Br)₃][Et₂NH₂], [{RuI(L)}₂(µ-I)₃][Et₂NH₂],

[RuCl[PPh₃](L)]₂(μ-Cl)₂, [RuBr[PPh₃](L)]₂(μ-Br)₂, [RuI[PPh₃](L)]₂(μ-I)₂, RuCl₂(L), RuBr₂(L), RuI₂(L), [RuCl₂(L)](dmf)ₙ, RuCl₂(L)(pyridine)₂, RuBr₂(L)(pyridine)₂, RuI₂(L)(pyridine)₂, RuCl₂(L)(2,2'-dipyridine), RuBr₂(L)(2,2'-dipyridine), RuI₂(L)(2,2'-dipyridine), [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [Ru(L)](OTf)₂, [Ru(L)](BF₄)₂, [Ru(L)](ClO₄)₂, [Ru(L)](SbF₆)₂, [Ru(L)](PF₆)₂, [Ru(L)](BPh₄)₂, [RuCl₂(L)](en), [RuBr₂(L)](en), [RuI₂(L)](en), [RuH₂(L)](en), [RuCl₂(L)](DPEN), [RuBr₂(L)](DPEN), [RuI₂(L)](DPEN), [RuH₂(L)](DPEN), [RuCl₂(L)](DAIPEN), [RuBr₂(L)](DAIPEN), [RuI₂(L)](DAIPEN), and [RuH₂(L)](DAIPEN), and RuCl₂(L), RuBr₂(L), and [RuCl₂(L)](dmf)ₙ are preferable.

Examples of the iridium catalyst having an optically active ligand include [IrL(cod)]Y and [IrL(nbd)]Y, and [IrL(cod)]Y is preferable. In the above-mentioned formula, Y represents an anion.

Examples of L in the iridium catalyst having an optically active ligand include, in addition to the above-mentioned L, optically active ligands of formula (3) to formula (24), and the optically active ligand is preferably an optically active ligand of formula (11-1), formula (11-2), formula (11-3), formula (11-4), formula (11-5), formula (11-6), or formula (11-7), and more preferably an optically active ligand of formula (11-7). A spatial structure of these optically active ligands is not limited to spatial structures shown below.

Formula (3):

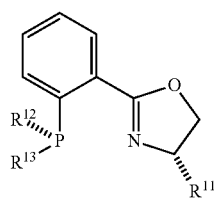

(3)

TABLE 1

| | $R^{11}$ | $R^{12}$ | $R^{13}$ |
|---|---|---|---|
| (3-1) | tert-butyl group | o-tolyl group | o-tolyl group |
| (3-2) | tert-butyl group | cyclohexyl group | cyclohexyl group |
| (3-3) | tert-butyl group | tert-butyl group | isopropyl group |
| (3-4) | tert-butylmethyl group | phenyl group | phenyl group |
| (3-5) | isopropyl group | phenyl group | phenyl group |

Formula (4):

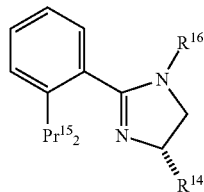

(4)

TABLE 2

| | $R^{14}$ | $R^{15}$ | $R^{16}$ |
|---|---|---|---|
| (4-1) | tert-butyl group | o-tolyl group | phenyl group |
| (4-2) | tert-butyl group | phenyl group | p-trifluorophenyl group |

Formula (5):

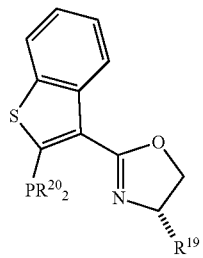

(5)

TABLE 3

| | $R^{17}$ | $R^{18}$ |
|---|---|---|
| (5-1) | tert-butyl group | cyclohexyl group |
| (5-2) | 1-adamantyl group | phenyl group |
| (5-3) | tert-butyl group | phenyl group |

Formula (6):

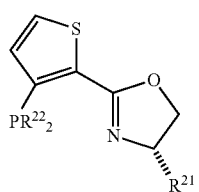

(6)

TABLE 4

| | $R^{19}$ | $R^{20}$ |
|---|---|---|
| (6-1) | isopropyl group | o-tolyl group |
| (6-2) | tert-butyl group | phenyl group |

Formula (7):

(7)

TABLE 5

| | $R^{21}$ | $R^{22}$ |
|---|---|---|
| (7-1) | tert-butyl group | cyclopropyl group |
| (7-2) | isopropyl group | phenyl group |

Formula (8):

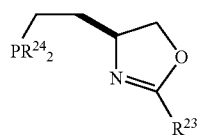

(8)

TABLE 6

| | $R^{23}$ | $R^{24}$ |
|---|---|---|
| (8-1) | methyl group | phenyl group |
| (8-2) | tert-butyl group | phenyl group |
| (8-3) | tert-butyl group | o-tolyl group |

Formula (9):

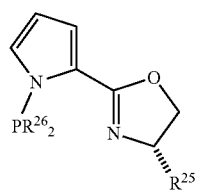

(9)

TABLE 7

| | $R^{25}$ | $R^{26}$ |
|---|---|---|
| (9-1) | tert-butyl group | o-tolyl group |
| (9-2) | tert-butyl group | cyclohexyl group |

Formula (10):

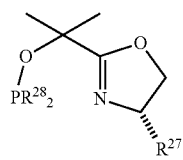

(10)

TABLE 8

| | $R^{27}$ | $R^{28}$ |
|---|---|---|
| (10-1) | tert-butyl group | o-tolyl group |
| (10-2) | isopropyl group | o-tolyl group |
| (10-3) | isopropyl group | phenyl group |
| (10-4) | tert-butyl group | phenyl group |

Formula (11):

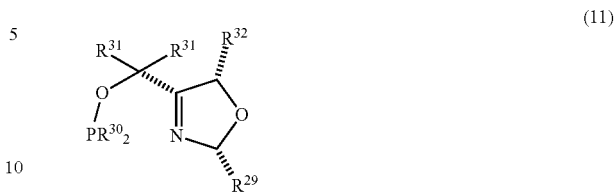

(11)

TABLE 9

| | $R^{29}$ | $R^{30}$ | $R^{31}$ | $R^{32}$ |
|---|---|---|---|---|
| (11-1) | phenyl group | phenyl group | benzyl group | methyl group |
| (11-2) | 3,5-dimethyl-phenyl group | phenyl group | benzyl group | methyl group |
| (11-3) | 3,5-di-tert-butyl-phenyl group | phenyl group | benzyl group | methyl group |
| (11-4) | phenyl group | phenyl group | n-butyl group | hydrogen atom |
| (11-5) | 3,5-di-tert-butyl-phenyl group | phenyl group | n-butyl group | hydrogen atom |
| (11-6) | phenyl group | cyclohexyl group | benzyl group | hydrogen atom |
| (11-7) | phenyl group | cyclohexyl group | benzyl group | methyl group |

Formula (12):

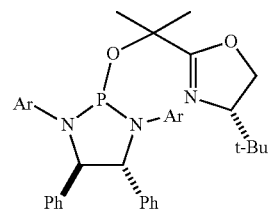

(12)

TABLE 10

| | Ar |
|---|---|
| (12-1) | 4-hydroxymethylphenyl group |
| (12-2) | biphenyl-4-yl |

Formula (13):

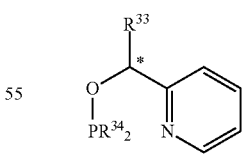

(13)

TABLE 11

| | $R^{33}$ | $R^{34}$ |
|---|---|---|
| (13-1) | tert-butyl group | tert-butyl group |
| (13-2) | phenyl group | phenyl group |
| (13-3) | tert-butyl group | o-tolyl group |
| (13-4) | phenyl group | tert-butyl group |

Formula (14):

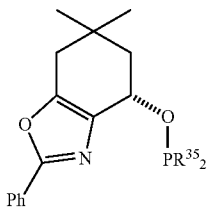
(14)

TABLE 12

| | $R^{35}$ |
|---|---|
| (14-1) | phenyl group |
| (14-2) | o-tolyl group |
| (14-3) | 3,5-dimethylphenyl group |

Formula (15):

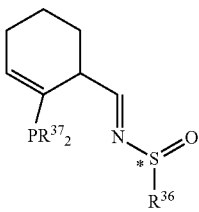
(15)

TABLE 13

| | $R^{36}$ | $R^{37}$ |
|---|---|---|
| (15-1) | (R)-tert-butyl group | o-tolyl group |
| (15-2) | (S)-mesityl group | o-tolyl group |

Frmula (16) to Frmula (24):

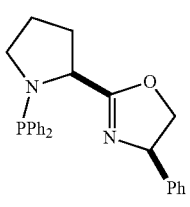
(16)

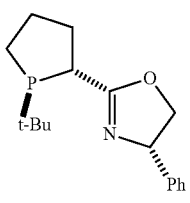
(17)

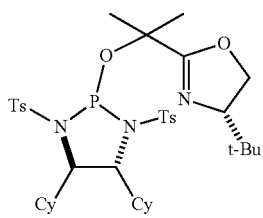
(18)

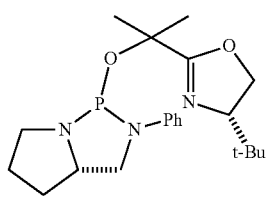
(19)

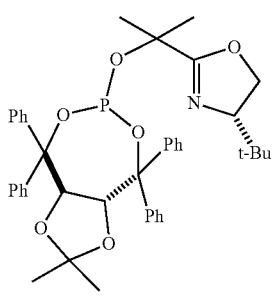
(20)

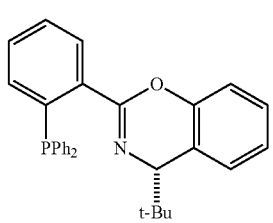
(21)

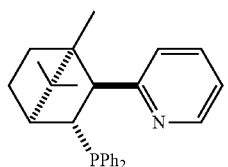
(22)

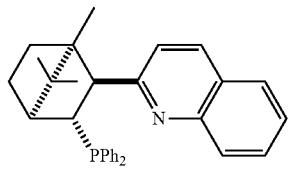
(23)

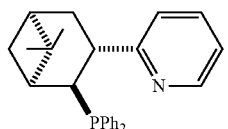
(24)

wherein Ph represents a phenyl group, Cy represents a cyclohexyl group, Is represents a tosyl group, and t-Bu represents a tert-butyl group.

Examples of Y include an anion represented by formulas (a) to (c), $PF_6^-$, $BF_4^-$, and $CF_3SO_3^-$, and an anion of formula (a) is preferable.

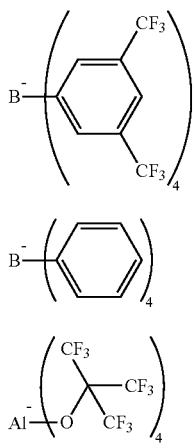

The amount of the transition metal catalyst to be used is usually in a range of 0.00001 to 0.2 mol, preferably 0.0005 to 0.1 mol, and still more preferably 0.001 to 0.05 mol, based on 1 mol of the compound (1). Two or more transition metal catalysts may be used.

Commercially available products may be used as the transition metal catalyst, and the transition metal catalyst may be manufactured in accordance with the method mentioned, for example, in JP 2002-187895 A. $RuCl_2[(R,R)\text{-}Me\text{-}DUPHOS](dmf)_n$, may be manufactured by the method mentioned in Forman, G. S.; Okuma, T.; Hem, W. P.; Noyori, R. Tetrahedron Lett. 2000, 41, 9471-9475.

Hydrogen is preferably a hydrogen gas.

Contact between a compound (1) and hydrogen in the presence of a transition metal catalyst is usually performed by mixing the transition metal catalyst, the compound (1), and hydrogen. Mixing is preferably performed by mixing the compound (1) with the transition metal catalyst, and then mixing the mixture thus obtained with a hydrogen gas.

After mixing with the hydrogen gas, the pressure in a reactor vessel is usually set in a range of 0.1 MPa to 20 MPa, preferably 0.1 MPa to 5 MPa, and more preferably 0.1 MPa to 1 MPa, in terms of a gauge pressure (hereinafter sometimes referred to as a gauge pressure).

The temperature at which contact between the compound (1) and hydrogen in the presence of the transition metal catalyst is performed is usually 20° C. or higher, preferably 40° C. or higher, and more preferably 60° C. or higher. The contact temperature is usually 100° C. or lower, preferably 90° C. or lower, and more preferably 80° C. or lower.

The time period during which contact between the compound (1) and hydrogen in the presence of the transition metal catalyst is performed is usually in a range of 0.1 to 100 hours, and preferably 0.1 to 48 hours.

Contact between the compound (1) and hydrogen in the presence of the transition metal catalyst may be performed in the presence of a solvent, or may be performed in the absence of a solvent.

Examples of the solvent include an aromatic solvent such as benzene, toluene, xylene, or pyridine; a halogen-containing hydrocarbon solvent such as chloroform, dichloromethane, 1,2-dichloroethane, or chlorobenzene; an ester solvent such as ethyl acetate; a ketone solvent such as acetone, methyl ethyl ketone, or methyl isobutyl ketone; an ether solvent such as 1,2-dimethoxyethane, diethylene glycol dimethyl ether, polyethylene glycol, tetrahydrofuran, or dioxane; a nitrile solvent such as acetonitrile or propylnitrile; a sulfoxide solvent such as dimethyl sulfoxide; an amide solvent such as dimethylacetamide or N-methylpyrrolidone; an alcohol solvent such as methanol, ethanol, or 2-propanol; a water solvent such as water, aqueous sodium hydroxide solution, or ammonia water; and a mixed solvent thereof. The solvent is preferably an alcohol solvent, a halogen-containing hydrocarbon solvent, or an aromatic solvent, more preferably hexane, trifluoroethanol, 1,2-dichloroethane, toluene, dichloromethane, or 2-propanol, and still more preferably dichloromethane or 2-propanol.

The amount of the solvent to be used is usually in a range of 1 to 100 parts by weight, and preferably 1 to 40 parts by weight, based on 1 part by weight of the compound (1).

Contact between the compound (1) and hydrogen in the presence of the transition metal catalyst may also be performed in the presence of an additive, and examples of the additive include an alkali metal alkoxide such as potassium tert-butoxide.

The additive may be used as a mixture with the solvent, and examples of the solvent include an alcohol solvent such as tert-butanol.

The amount of the additive to be used is usually in a range of 0.01 to 0.2 mol based on 1 mol of the compound (1).

A mixture containing a compound (2) is obtained by contact between the compound (1) and hydrogen in the presence of the transition metal catalyst. The thus obtained mixture is filtered to remove the transition metal catalyst, and the filtrate is concentrated, thereby obtaining the compound (2). The compound (2) thus obtained can also be purified by a known method such as crystallization or chromatography.

The transition metal catalyst removed by filtration is recovered and can be used again in the manufacture of the compound (2). Examples of the recovery method include a method in which the transition metal catalyst is supported on a carrier.

The transition metal catalyst having an optically active ligand may be prepared in a reaction system. In this case, the compound (2) can be obtained by mixing an optically active ligand L, a transition metal catalyst having no optically active ligand, a compound (1), and hydrogen.

Mixing of an optically active ligand L, a transition metal catalyst having no optically active ligand, a compound (1), and hydrogen is preferably performed by mixing an optically active ligand L, a transition metal catalyst having no optically active ligand, and a compound (1), and then mixing the mixture thus obtained with hydrogen.

Examples of the transition metal catalyst having no optically active ligand include $[RhCl(cod)]_2$, $[RhBr(cod)]_2$, $[RhI(cod)]_2$, $[RhOAc(cod)]_2$, $[RhOPh(cod)]_2$, $[Rh(cod)_2]BF_4$, $[RuCl(cod)]_2$, $[RuBr(cod)]_2$, $[RuI(cod)]_2$, $[RuOAc(cod)]_2$, $[RuOPh(cod)]_2$, and $[Ru(cod)_2]BF_4$.

When mixing an optically active ligand L, a transition metal catalyst having no optically active ligand, a compound (1), and hydrogen, the amount of L to be used is usually in a range of 0.00001 to 0.2 mol, and preferably 0.001 to 0.1 mol, based on 1 mol of the compound (1).

The amount of the transition metal catalyst having no optically active ligand to be used is usually in a range of 0.00001 to 0.2 mol, and preferably 0.001 to 0.1 mol, based on 1 mol of the compound (1).

EXAMPLES

Examples will be described below. In Examples, room temperature indicates a temperature in a range of 10 to 35°

C. Optical purity in Examples was determined by performing high performance liquid chromatographic analysis under the following conditions.
Column: Daicel CHIRALCEL OD-H (4.6 mmϕ×250 mm)
Eluent: hexane/2-propanol=99/1 (v/v)
Flow rate: 0.5 mL/minute
Temperature: 40° C.
Detector: UV at 254 nm A GC area percentage (A) of the compound (2) and an area percentage (B) of the unreacted compound (1) were measured by analysis of a mixture containing the compound (2) using gas chromatography under the following conditions.
Column: Agilent Technologies DB-5 (1.5 μm, 0.53 mmϕ×30 m)
Temperature: After maintaining an initial temperature of 100° C. for 5 minutes, the temperature was raised to a final temperature of 300° C. at 8° C./minute.
Injector: 250° C.
Detector: 300° C.

A conversion ratio was determined using the following calculation formula.

Conversion ratio (%)=(A)/((A)+(B))

A catalyst of the following structural formula is referred to as an iridium catalyst (1):

wherein Ph represents a phenyl group, Bn represents a benzyl group, and Cy represents a cyclohexyl group.

A compound of formula (1-1), a compound of formula (1-11), a compound of formula (2-1), and a compound of formula (2-11) respectively represent compounds of the following structure formula:

(1-1)

(1-11)

(2-1)

(2-11)

wherein Ac represents an acetyl group.

Example 1

In a reactor vessel, 1.0 g of a compound of formula (1-1), 19.36 g of toluene, and 10 mg of an iridium catalyst (1) were charged to obtain a mixture. After sealing the reactor vessel, a gas in the reactor vessel was replaced by nitrogen. While stirring the mixture, hydrogen was charged into the reactor vessel to an internal pressure of 0.7 MPa in gauge pressure. The inner temperature was raised to 70° C., followed by stirring for 8 hours. The reaction mixture thus obtained was cooled and filtered. The filtrate thus obtained was concentrated under reduced pressure to obtain 1.05 g of the mixture containing a compound of formula (2-1). The thus obtained compound of formula (2-1) exhibited an optical purity of 5.8% ee. A conversion ratio was 8.7%.

Example 2

In a reactor vessel, 1.0 g of a compound of formula (1-1), 19.36 g of dichloromethane, and 10 mg of an iridium catalyst (1) were charged to obtain a mixture. After sealing the reactor vessel, a gas in the reactor vessel was replaced by nitrogen. While stirring the mixture, hydrogen was charged into the reactor vessel to an internal pressure of 0.7 MPa in gauge pressure. The inner temperature was raised to 70° C., followed by stirring for 8 hours. The reaction mixture thus obtained was cooled and filtered. The filtrate thus obtained was concentrated under reduced pressure to obtain 1.11 g of the mixture containing a compound of formula (2-1). The thus obtained compound of formula (2-1) exhibited an optical purity of 11.6% ee. A conversion ratio was 3.5%.

Example 3

In a reactor vessel, 1.0 g of a compound of formula (1-1), 19.36 g of dichloromethane, and 10 mg of an iridium catalyst (1) were charged to obtain a mixture. After sealing the reactor vessel, a gas in the reactor vessel was replaced by nitrogen. While stirring the mixture, hydrogen was charged into the reactor vessel to an internal pressure of 0.7 MPa in gauge pressure. The inner temperature was raised to 70° C., followed by stirring for 8 hours. The reaction mixture thus obtained was cooled and filtered. The filtrate thus obtained was concentrated under reduced pressure to obtain 1.11 g of the mixture containing a compound of formula (2-1). The

Example 4

In a reactor vessel, 0.5 g of a compound of formula (1-1), 16.77 g of trifluoroethanol, and 50 mg of an iridium catalyst (1) were charged to obtain a mixture. After sealing the reactor vessel, a gas in the reactor vessel was replaced by nitrogen. While stirring the mixture, hydrogen was charged into the reactor vessel to an internal pressure of 0.9 MPa in gauge pressure. The inner temperature was raised to 40° C., followed by stirring for 9 hours. The reaction mixture thus obtained was cooled and filtered. The filtrate thus obtained was concentrated under reduced pressure to obtain 0.66 g of the mixture containing a compound of formula (2-1). The thus obtained compound of formula (2-1) exhibited an optical purity of 44.6% ee. A conversion ratio was 6.5%.

Example 5

In a reactor vessel, 0.5 g of a compound of formula (1-1), 16.77 g of dichloromethane, and 50 mg of an iridium catalyst (1) were charged to obtain a mixture. After sealing the reactor vessel, a gas in the reactor vessel was replaced by nitrogen. While stirring the mixture, hydrogen was charged into the reactor vessel to an internal pressure of 0.9 MPa in gauge pressure. The inner temperature was raised to 40° C., followed by stirring for 9 hours. The reaction mixture thus obtained was cooled and filtered. The filtrate thus obtained was concentrated under reduced pressure to obtain 0.60 g of the mixture containing a compound of formula (2-1). The thus obtained compound of formula (2-1) exhibited an optical purity of 71.3% ee. A conversion ratio was 62.6%.

Example 6

In a reactor vessel, 0.5 g of a compound of formula (1-11), 16.77 g of trifluoroethanol, and 50 mg of an iridium catalyst (1) were charged to obtain a mixture. After sealing the reactor vessel, a gas in the reactor vessel was replaced by nitrogen. While stirring the mixture, hydrogen was charged into the reactor vessel to an internal pressure of 0.7 MPa in gauge pressure. The inner temperature was raised to 90° C., followed by stirring for 9 hours. The reaction mixture thus obtained was cooled and filtered. The filtrate thus obtained was concentrated under reduced pressure to obtain 0.60 g of the mixture containing a compound of formula (2-11). The thus obtained compound of formula (2-11) exhibited an optical purity of 31.3% ee. A conversion ratio was 14.3%.

Example 7

In a reactor vessel, 0.5 g of a compound of formula (1-11), 16.77 g of dichloromethane, and 50 mg of an iridium catalyst (1) were charged to obtain a mixture. After sealing the reactor vessel, a gas in the reactor vessel was replaced by nitrogen. While stirring the mixture, hydrogen was charged into the reactor vessel to an internal pressure of 0.7 MPa in gauge pressure. The inner temperature was raised to 70° C., followed by stirring for 10 hours. The reaction mixture thus obtained was cooled and filtered. The filtrate thus obtained was concentrated under reduced pressure to obtain 0.58 g of the mixture containing a compound of formula (2-11). The thus obtained compound of formula (2-11) exhibited an optical purity of 31.8% ee. A conversion ratio was 4.0%.

Example 8

Under a nitrogen atmosphere, 100 mg of (R,R)-Me-DuPhos and 85 mg of $[RuCl_2(C_6H_6)]_2$ were dissolved in 2 mL of dimethylformamide. The mixture thus obtained was stirred at 100° C. for 2 hours. The reaction mixture thus obtained was concentrated under reduced pressure. To the residue thus obtained, 2.5 mL of diethyl ether and 2.5 mL of dichloromethane were added, followed by filtration. The filtrate thus obtained was concentrated and 3 mL of hexane was added, followed by filtration. The filtrate thus obtained was concentrated and the solid was filtered. The solid thus obtained was washed with 1 mL of hexane to obtain 23.4 mg of $RuCl_2[(R,R)$-Me-DUPHOS$](dmf)_n$. In a reactor vessel, 0.5 g of a compound of formula (1-1), 19.16 g of 2-propanol, 0.2 mL of a tert-butanol solution of 1M potassium tert-butoxide, and 8.6 mg of the thus obtained $RuCl_2[(R,R)$-Me-DUPHOS$](dmf)_n$ were charged. After sealing the reactor vessel, a gas in the reactor vessel was replaced by nitrogen. While stirring the mixture, hydrogen was charged into the reactor vessel to an internal pressure of 0.9 MPa in gauge pressure. The inner temperature was raised to 65° C., followed by stirring for 9 hours. The reaction mixture thus obtained was cooled and filtered. The filtrate thus obtained was concentrated under reduced pressure to obtain 0.51 g of the mixture containing a compound of formula (2-1). The thus obtained compound of formula (2-1) exhibited an optical purity of 5.3% ee. A conversion ratio was 13.5%.

Example 9

In a reactor vessel, 0.5 g of a compound of formula (1-1), 19.16 g of dichloromethane, 51 mg of chloro(1,5-cyclooctadiene)rhodium(I) (dimer), and 155 mg of (S)-2,2'-bis(diphenylphosphino)-1,1'-binaphthyl were charged to obtain a mixture. After sealing the reactor vessel, a gas in the reactor vessel was replaced by nitrogen. While stirring the mixture, hydrogen was charged into the reactor vessel to an internal pressure of 0.7 MPa in gauge pressure. The inner temperature was raised to 70° C., followed by stirring for 8.5 hours. The reaction mixture thus obtained was cooled and filtered. The filtrate thus obtained was concentrated under reduced pressure to obtain 0.60 g of the mixture containing a compound of formula (2-1). The thus obtained compound of formula (2-1) exhibited an optical purity of 59.1% ee. A conversion ratio was 16.3%.

Example 10

In a reactor vessel, 0.5 g of a compound of formula (1-1), 19.16 g of dichloromethane, 51 mg of chloro(1,5-cyclooctadiene)rhodium(I) (dimer), and 155 mg of (R)-2,2'-bis(diphenylphosphino)-1,1'-binaphthyl were charged to obtain a mixture. After sealing the reactor vessel, a gas in the reactor vessel was replaced by nitrogen. While stirring the mixture, hydrogen was charged into the reactor vessel to an internal pressure of 0.7 MPa in gauge pressure. The inner temperature was raised to 70° C., followed by stirring for 9 hours. The reaction mixture thus obtained was cooled and filtered. The filtrate thus obtained was concentrated under reduced pressure to obtain 0.53 g of the mixture containing a compound of formula (2-1). The thus obtained compound of formula (2-1) exhibited an optical purity of 56.0% ee. A conversion ratio was 14.7%.

INDUSTRIAL APPLICABILITY

According to the invention, it is possible to manufacture an optically active compound of formula (2) by asymmetric hydrogenation of a compound of formula (1).

The invention claimed is:

1. A method for manufacturing an optically active compound of formula (2):

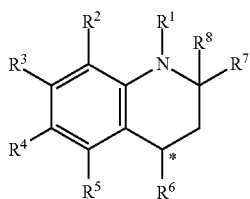

(2)

wherein $R^1$, $R^2$, $R^3$, $R^4$, $R^5$, $R^6$, $R^7$, and $R^8$ are the same as defined below, and a carbon atom marked with an asterisk (*) represents an asymmetric carbon atom, which comprises bringing hydrogen into contact with a compound of formula (1):

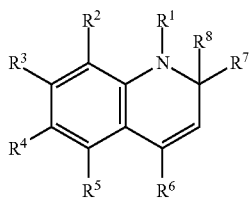

(1)

wherein $R^1$ represents a hydrogen atom or an acetyl group, $R^2$, $R^3$, $R^4$, and $R^5$ each independently represents a hydrogen atom, a halogen atom, an alkyl group, an alkoxy group, a hydroxy group, a nitro group, an amino group, or an acyl group, $R^6$ represents an alkyl group, and $R^7$ and $R^8$ each independently represents a hydrogen atom or an alkyl group, in the presence of a transition metal catalyst having an optically active ligand.

2. The manufacturing method according to claim 1, wherein $R^6$ is a methyl group or an ethyl group, and $R^7$ and $R^8$ are each independently a hydrogen atom, a methyl group, or an ethyl group.

3. The manufacturing method according to claim 1, wherein $R^6$, $R^7$, and $R^8$ are methyl groups, and $R^2$, $R^3$, $R^4$, and $R^5$ are hydrogen atoms.

4. The manufacturing method according to claim 1, wherein the transition metal catalyst having an optically active ligand is an iridium catalyst having an optically active ligand, a rhodium catalyst having an optically active ligand, or a ruthenium catalyst having an optically active ligand.

5. The manufacturing method according to claim 1, wherein hydrogen is brought into contact with the compound of formula (1) at a temperature in a range of 20 to 100° C.

6. The manufacturing method according to claim 1, wherein hydrogen is brought into contact with the compound of formula (1) under a gauge pressure in a range of 0.1 MPa to 20 MPa.

* * * * *